United States Patent [19]

Leupold et al.

[11] 4,442,228

[45] Apr. 10, 1984

[54] PROCESS FOR THE MANUFACTURE OF ETHANOL FROM SYNTHESIS GAS

[75] Inventors: Ernst I. Leupold, Neu-Anspach; Hans-Joachim Schmidt, Königstein; Friedrich Wunder, Flörsheim am Main; Hans-Jürgen Arpe, Kelkheim; Horst Hachenberg, Walluf, all of Fed. Rep. of Germany

[73] Assignee: Hoechst Aktiengesellschaft, Frankfurt am Main, Fed. Rep. of Germany

[21] Appl. No.: 443,131

[22] Filed: Nov. 19, 1982

Related U.S. Application Data

[63] Continuation of Ser. No. 289,706, Aug. 3, 1981, abandoned, which is a continuation of Ser. No. 86,952, Oct. 22, 1979, abandoned.

[30] Foreign Application Priority Data

Oct. 24, 1978 [DE] Fed. Rep. of Germany ....... 2846148

[51] Int. Cl.$^3$ ..................... C07C 27/06; C07C 31/08
[52] U.S. Cl. ................................... 518/714; 518/716; 502/303; 502/313; 502/326; 502/328

[58] Field of Search ................................. 518/714, 716

[56] References Cited

U.S. PATENT DOCUMENTS 3,833,634  9/1974  Pruett et al. .
4,116,994  9/1978  Vanniu et al. .
4,122,110  10/1978  Sugier .
4,224,236  9/1980  Wunder et al. .
4,228,558  9/1981  Schmidt et al. .

OTHER PUBLICATIONS

Ichikawa, Bull. Chem. Soc., Japan, vol. 51 (8), 2273–2277, (1978).
Ichikawa, J.C.S. Chem. Comm., (1978), pp. 566–567.

*Primary Examiner*—Howard T. Mars
*Attorney, Agent, or Firm*—Curtis, Morris & Safford

[57] ABSTRACT

Ethanol is manufactured by reaction of carbon monoxide with hydrogen on a supported rhodium catalyst containing as cocatalyst at least one of the elements zirconium, hafnium, lanthanum, platinum, chromium and mercury.

7 Claims, No Drawings

PROCESS FOR THE MANUFACTURE OF ETHANOL FROM SYNTHESIS GAS

This is a continuation, of application Ser. No. 289,706 filed Aug. 3, 1981 abandoned, which is a continuation of application Ser. No. 086,952, filed Oct. 22, 1979, abandoned.

This invention relates to a process for the manufacture of ethanol by reaction of carbon monoxide with hydrogen on a supported rhodium catalyst.

It is known from German Auslegeschriften DE-AS Nos. 2,503,233 and 2,628,463 that the gas phase reaction of synthesis gas in the presence of catalysts containing metallic rhodium yield substantially mixtures of oxygen-containing compounds having two carbon atoms in the molecule, such as acetic acid, ethanol and acetaldehyde.

It is further known from DE-AS No. 2,503,204 that the selectivity of ethanol can be increased by the addition of iron salts. However, addition of iron salts reduces the activity of the rhodium catalyst considerably. According to Table 1 of DE-AS No. 2,503,204 the space-time-yields with iron-containing rhodium catalysts are about 4 times lower than that of an iron-free rhodium catalyst used for comparison. With regard to the economy of a process such a decrease in the yield with regard to the formation of oxygen-containing $C_2$-compounds is extremely unsatisfactory.

From U.S. Pat. No. 4,096,164 it is known that the selectivity with respect to the formation of alcohols can be generally increased by adding molybdenum or tungsten to rhodium-containing catalysts. However, use of these two cocatalysts does not result in a substantially increased formation of ethanol since larger amounts of methanol, propanol and butanol are formed.

It is, therefore, an object of the present invention to improve the ethanol selectivity of rhodium catalysts, by minimizing the formation of other compounds such as methanol, propanol and butanol without realizing a decrease in the space-time-yield of ethanol.

It has now been found that the ethanol selectivity and space-time-yield of ethanol can be substantially improved by using rhodium catalysts additionally containing, applied onto a carrier, at least one of the elements zirconium, hafnium, lanthanum, platinum, chromium and mercury.

The present invention thus provides a process for the manufacture of ethanol by reaction of carbon monoxide with hydrogen in the presence of a supported rhodium catalyst, which comprises using as cocatalyst at least one of the elements zirconium, hafnium, lanthanum, platinum, chromium and mercury.

The discovery that the composition of the reaction product can be shifted by the use of the aforesaid elements in favor of ethanol with a simultaneous increase in the space-time-yield is surprising.

In addition to ethanol, which is formed with a high selectivity in the process of the invention, smaller amounts of other oxygen-containing $C_2$-compounds are formed, such as acetaldehyde and acetic acid and other products which can be formed from these compounds in a secondary reaction, for example by esterification, acetalization or condensation. Compounds of the latter type are, inter alia, ethyl acetate and the diethyl acetal of acetaldehyde. The proportion of other oxygen-containing compounds having three or more carbon atoms in the molecule is very low and generally it is below 5 mol %, calculated on reacted carbon monoxide. The total selectivity for oxygen-containing $C_2$-compounds, including the products converted into ethyl acetate and acetaldehyde diethyl acetal, is up to 81%, calculated on the reacted carbon monoxide. The remainder of the carbon monoxide is converted into the aforesaid products having 3 and more carbon atoms and in addition essentially into methane and other gaseous hydrocarbons and a small proportion of carbon dioxide.

For synthesis of the catalyst used in the process of the present invention, salts or complex compounds of rhodium can be used, for example chlorides, bromides and iodides as well as double salts of rhodium with alkali metal halides, for example dipotassium-trichlororhodate. There are also suitable complex compounds containing, besides rhodium and halogen, complex-forming ligands, such as trialkyl-phosphines, triaryl-phosphines, ethylene diamine, pyridine, carbon monoxide, olefins or water. Compounds of this type are, for example, tristriphenylphosphine-rhodium-I-chloride, -bromide- or iodide, tristriphenylphosphine-rhodium-III-chloride, dichloro-bisethylene-diamine-rhodium-I-chloride, trisethylenediamine-rhodium-III-chloride, bis-tri-o-tolylphosphine-rhodium-II-chloride, carbonyl-bistriphenylphosphine-rhodium-I-bromide or dicesiumcarbonylpentachlororhodate-III. In addition, compounds of rhodium can be used in which they are bound to a carrier by ion or complex bonds, such as zeolites and ion exchangers which have been exchanged with rhodium halides.

As a cocatalyst in the process of the invention there is used at least one of the elements zirconium, hafnium, lanthanum, platinum, chromium and mercury applied onto the carrier in the form of their salts or complex compounds. Zirconium, hafnium, lanthanum, chromium or mercury are preferred and more preferably hafnium, chromium or mercury are used. The elements can be used in the form of simple inorganic or organic salts, for example the chlorides, bromides, nitrates, formates, acetates, preferably, however, the chlorides. The oxides, hydroxides or carbonates can also be used, provided that they are converted into the aforesaid salts by a treatment with mineral acids or carboxylic acids. Especially suitable complex compounds are chloro-complexes of rhodium of the formula $M_m[RhCl_6]_n$ in which M denotes the element of the cocatalyst, in the case of chromium, for example, the complex $Cr[RhCl_6]\cdot 2H_2O$, which can be obtained by reacting chromium chloride with rhodium chloride at 100° C. in acetic acid.

Complexes of the aforesaid type can be applied onto the carrier by impregnation. Because of the poor solubility of some complexes it is often advantageous to impregnate the carrier with a solution of rhodium-III-chloride and one or several chlorides of the elements named as cocatalysts in acetic acid and subsequently to heat the treated carrier to a temperature of 100° C., whereupon the complexes form in the pores. Alternatively, the element acting as cocatalyst can be applied to the carrier first or it can be incorporated into a skeleton substance, for example a carrier material containing a silicate or aluminum oxide, for example silicic acid, aluminum oxide or aluminum silicate. A further advantageous method consists in binding the cations of the elements acting as cocatalysts by means of ion exchange to a cation exchanger which can also be used as carrier for the rhodium and which is stable under the reaction conditions, for example natural or synthetic aluminum silicates known as molecular sieves. Suitable catalysts can also be obtained when the carrier is impregnated in the reverse order of succession, i.e. first with a rhodium compound and then with the respective cocatalyst. The catalyst efficiency with an unchanged high selectivity for ethanol can be further improved by adding other promoters, especially magnesium.

Suitable catalyst carriers are the usual carrier materials having different specific surfaces. Carriers having a specific surface in the range of from 50 to 1,000 m$^2$/g are preferred. Suitable materials are, for example, silicic acid, natural or synthetic silicates of elements of groups II to VIII of the Periodic Table (that is, for example, the silicates of magnesium, calcium, aluminum, manganese), furthermore aluminum dioxide, thorium dioxide, zeolites and spinels. Silicic acid and silicates are preferred.

For the manufacture of the catalysts the carrier material is impregnated with the active components either simultaneously or successively. When rhodium-III-salts are used, a subsequent treatment with a suitable reducing agent such as hydrogen, carbon monoxide or methanol proved advantageous. This reduction can be carried out in a separate apparatus or in the reactor itself. In general, the temperatures applied in the reduction are below 300° C., preferably in the range of from 100 to 275° C. In many cases it is expedient to carry out the reduction not with the undiluted reducing gases but with a gas mixture additionally containing an inert gas, for example nitrogen, carbon dioxide or a noble gas.

It is likewise possible to produce the carrier material in the presence of the active components, for example by concomitant precipitation of the active components with silicates.

The concentration of rhodium and cocatalyst in the catalysts can vary within wide limits. In general, a catalyst contains 0.1 to 20% by weight of rhodium and 0.1 to 25% by weight of cocatalyst, preferably 1.0 to 10% by weight of rhodium and 0.1 to 20% by weight of cocatalyst.

To carry out the process of the invention a gas mixture wholly or substantially consisting of carbon monoxide and hydrogen and possibly containing other components such as nitrogen, argon, carbon dioxide, or methane is passed over the catalyst. The molar proportion of carbon monoxide to hydrogen can be varied in wide limits. Molar proportions of from 5:1 to 1:5 and especially 3:1 to 1:3 are preferred. In general, the reaction temperatures are in the range of from 175° C. to 375° C., preferably 200° C. to 350° C. and the reaction pressure ranges from 1 to 300 bar, preferably 20 to 200 bar.

Temperature and pressure should be adjusted in such a manner that a high selectivity for the oxygen-containing compounds is ensured while the exothermal formation of methane which is favored by elevated temperatures is kept low. Therefore, high pressures and low temperatures will be preferred. The conversion of carbon monoxide should not exceed 50%, in general, since a higher conversion may readily lead to the formation of an increased amount of byproducts consisting not only of methane, carbon dioxide and gaseous hydrocarbons but also of liquid hydrocarbons of higher molecular weight and oxygen-containing products.

The process is preferably carried out in the gaseous phase. Conventional fixed bed reactors can be used in which, for a satisfactory dissipation of heat, the catalyst is used in thin layers. Reactors with moved catalyst bed or fluidized bed reactors can also be used.

Alternatively, the reaction of synthesis gas can be carried out in the presence of a suspension of the solid and finely dispersed catalyst in inert media and/or reaction products.

According to an especially preferred embodiment of the invention, the reaction is carried out in the gaseous phase in an apparatus with gas circulation from which, after separation of the condensible reaction products, the unreacted gas mixture is recycled into the reactor.

This mode of operation is particularly economic. Due to the fact that the fresh gas is diluted with the recycled residual gas having a lower hydrogen content, higher reaction temperatures can be used so that higher space-time-yields are obtained with an unchanged selectivity. As apparatus with gas circulation those with internal or external gas cycle can be used.

The following examples illustrate the invention, but they are not intended to limit it thereto.

EXAMPLES (A) General description of the test

The apparatus used consists of a heated reaction tube, having a length of 1 meter and an inner diameter of 16 millimeters and made of corrosion-resistant steel, with a coaxially fitted housing for a thermometer having an outer diameter of 6 mm, a following condenser, a receiver for the condensate and a compressor for recycling a portion of the non condensed gas to the reactor (cycle gas). In each test the reactor is charged with 100 ml of the catalysts defined below. After flushing the apparatus with nitrogen, first a pressure of 100 bar is obtained with a synthesis gas consisting of 49% by volume of CO, 49% by volume of H$_2$, 1% by volume of CO$_2$, 1% by volume of N$_2$ and minor amounts of other components and the reactor is heated to 275° C. During heating and during the course of the test 450 normal liters of synthesis gas having the aforesaid compositions are added to the cycle gas over the suction side of the compressor and the mixture is passed over the catalyst. The gas mixture leaving the reactor is cooled to about +5° C. in the condenser cooled with brine and the condensed fractions are collected in the receiver. After the addition of fresh synthesis gas, the non condensed residual gas is returned to the reactor via the compressor. To maintain the pressure and to remove by-products part of the residual gas is branched of as exhaust gas via a pressure regulating valve. All catalysts defined below are tested by this method. The table below indicates the duration of the tests, the space-time-yields of oxygen-containing C$_2$-compounds per liter of catalyst and hour as well as the selectivities for ethanol, acetaldehyde and acetic acid (in mol % of CO, calculated on reacted CO). Minor amounts of ethyl acetate and acetaldehyde diethyl acetal formed are calculated as acetic acid, ethanol and acetaldehyde.

(B) Preparation of the catalyst

Each time 40 g of silicic acid having a BET surface of 270 m$^2$/g, a pore volume of 1.27 ml/g and an apparent density of 0.4 kg/l are impregnated with a solution of 5.2 g of RhCl$_3$.$\times$H$_2$O (38.0% by weight of Rh) in 50 ml of water and dried for 1.5 hours at 80° C., for 1.5 hours at 110° C. and for 1.5 hours at 150° C.

This catalyst is used for the comparative Example.

For Examples 1 to 7 the catalyst obtained is further impregnated with an aqueous or alcoholic solution of the following chlorides, each time in 50 ml of solvent, and dried for 2 hours at 80° C. and then for 2 hours at 150° C.

| Example no. | cocatalyst | amount in g |
| --- | --- | --- |
| 1 | Zr Cl$_4$ | 3.4 |
| 2 | La Cl$_3$ | 4.8 |
| 3 | Pt Cl$_4$ | 4.9 |
| 4 | Cr Cl$_3$.6 H$_2$O | 5.2 |
| 5 | Hf Cl$_4$ | 4.7 |
| 6 | Hg Cl$_2$ | 7.9 |
| 7 | Zr Cl$_4$ + Mg Cl$_2$.6 H$_2$O | 3.4 + 0.3 |

Next, the catalysts for Example 1 to 7 obtained are heated for 5 hours to 100° C. in a glass flask with a reflux condenser together with 50ml of acetic acid and then dried for 1.5 hours at 110° C., for 3 hours at 150° C. and finally for 1 hour at 300° C. under nitrogen.

The cataysts for examples 1 to 7 are then reduced in a flow tube made of glass by passing over 30 Nl/hr of hydrogen for 3 hours at 225° to 275° C., under atmospheric pressure.

(C) Test results

The results obtained are summarized in the following table. The indicated values are average values obtained with reaction times of 100 hours each.

TABLE

Reaction conditions: apparatus with gas circulation, 100 bar, 275° C., feed gas 400 Nl/hr with CO:H$_2$ ratio of 1:1, catalyst volume 0.1 l, duration of test 100 hours (AcOH acetic acid, AcH acetaldehyde, EtOH ethanol)

| Example No. | catalyst | space-time-yield in g/l · hr | | selectivity (mol % CO)* | | | |
| --- | --- | --- | --- | --- | --- | --- | --- |
| | | $\Sigma C_2$—O | EtOH | AcOH | AcH | EtOH | $\Sigma C_2$—O |
| Comparative example | Rh | 52 | 31 | 17.2 | 6.4 | 24.4 | 48.0 |
| 1 | Rh/Zr | 390 | 343 | 4.1 | 1.8 | 70.1 | 76.0 |
| 2 | Rh/La | 380 | 318 | 7.0 | 4.0 | 67.5 | 78.5 |
| 3 | Rh/Pt | 350 | 320 | 3.2 | 2.4 | 75.0 | 80.6 |
| 4 | Rh/Cr | 390 | 351 | 5.4 | 3.5 | 68.1 | 77.0 |
| 5 | Rh/Hf | 360 | 311 | 6.4 | 2.2 | 66.4 | 75.0 |
| 6 | Rh/Hg | 375 | 340 | 4.0 | 2.5 | 74.5 | 81.0 |
| 7 | Rh/Zr/Mg | 475 | 420 | 4.8 | 2.8 | 69.9 | 77.5 |

*mol % calculated on reacted carbon monoxide

The space-time-yield (STY) is given in gram per liter of catalyst and hour; in the first column the STY of oxygen-containing C$_2$-compounds, i.e. acetic acid, acetaldehyde and ethanol is given ($\Sigma C_2$-O) and in the second column the STY of ethanol alone (EtOH)

What is claimed is:

1. In a catalytic process for the manufacture of ethanol by catalytically reacting carbon monoxide and hydrogen in the presence of a supported rhodium catalyst at a temperature in the range of 175° C. to 375° C. and a pressure in the range of 1 to 300 bar, the improvement which comprises selecting a supported rhodium catalyst consisting of an rhodium component and at least one co-catalyst selected from the group consisting of zirconium, hafnium, lanthanum, platinum, chromium and mercury wherein said rhodium component and co-catalyst are applied by impregnation onto a catalyst carrier of silicic acid or silicates of elements of groups II to VIII of the Periodic Table.

2. The process of claim 1 wherein said catalyst contains 0.1 to 20% by weight rhodium and 0.1 to 25% by weight co-catalyst.

3. The process of claim 1 wherein said catalyst contains 1.0 to 10% by weight rhodium and 0.1 to 20% by weight co-catalyst.

4. The process of claim 1 wherein the molar ratio of carbon monoxide to hydrogen is in the range of about 5:1 to 1:5.

5. The process of claim 1 wherein the catalyst is a complex compound of the co-catalyst containing a chloro-complex of rhodium as an ion.

6. The process of claim 1 wherein said complex compound is Cr[RhCl$_6$].2H$_2$O.

7. The process of claim 1 wherein an effective amount of magnesium is added as catalytic promotor to said catalyst.

* * * * *